United States Patent
Lenhard et al.

(10) Patent No.: US 8,420,806 B2
(45) Date of Patent: Apr. 16, 2013

(54) PROCESS FOR THE CRYSTALLISATION OF CEFADROXIL MONOHYDRATE

(75) Inventors: Carlos Enrique Lenhard, Alella Barcelona (ES); Harold Monro Moody, Gulpen (NL); Theodorus Johannes Godfried Maria Van Dooren, Roermond (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 617 days.

(21) Appl. No.: 12/300,046

(22) PCT Filed: May 11, 2007

(86) PCT No.: PCT/EP2007/054572
§ 371 (c)(1),
(2), (4) Date: Sep. 30, 2009

(87) PCT Pub. No.: WO2007/134987
PCT Pub. Date: Nov. 29, 2007

(65) Prior Publication Data
US 2010/0010213 A1      Jan. 14, 2010

(30) Foreign Application Priority Data

May 19, 2006    (EP) ..................................... 06114240

(51) Int. Cl.
*C07D 501/22*    (2006.01)
*A61K 31/546*    (2006.01)

(52) U.S. Cl.
USPC ........................................................ 540/230

(58) Field of Classification Search ............... 540/230; 514/209
See application file for complete search history.

(56) References Cited

U.S. PATENT DOCUMENTS

| | | | |
|---|---|---|---|
| 3,489,752 A * | 1/1970 | Crast, Jr. ................... | 540/228 |
| 3,781,282 A * | 12/1973 | Garbrecht ................... | 540/220 |
| 3,985,741 A * | 10/1976 | Crast et al. ................ | 540/230 |
| 4,091,215 A | 5/1978 | Bouzard et al. | |
| 4,223,135 A | 9/1980 | Walker et al. | |
| 4,504,657 A * | 3/1985 | Bouzard et al. ............. | 540/230 |
| 4,904,776 A * | 2/1990 | Marsili ..................... | 540/230 |
| 5,329,001 A * | 7/1994 | Marsili ..................... | 540/230 |
| 5,840,885 A * | 11/1998 | Diago et al. ............... | 540/222 |

FOREIGN PATENT DOCUMENTS

| | | |
|---|---|---|
| EP | 0 295 333 | 12/1988 |
| ES | 2010288 A6 * | 11/1989 |
| WO | 99/24441 | 5/1999 |
| WO | WO 9955710 A1 * | 11/1999 |
| WO | 2004/035593 | 4/2004 |

OTHER PUBLICATIONS

"X-Rite® 918 Tristimulus Reflection Colorimeter" <http://www.xrite.com/documents/manuals/en/918-500_918_Operation_Manual_en.pdf> [retrieved from the internet Jan. 6, 2012].*
Gong, Jun-bo, "Study on the reactive crystallization of cefadroxil", Zhongguo Kangshengsu Zazhi (2005), 30(1), 62-64, S1.*
Translation of Gong, Jun-bo, "Study on the reactive crystallization of cefadroxil", Zhongguo Kangshengsu Zazhi (2005), 30(1), 62-64, S1.*
Ampicillin, The Merck Index—An Encyclopedia of Chemicals, Drugs, and Biologicals (14th Edition—Version 14.9), 2006.*
Leitner, Infection vol. 8, Supplement—5 (1980), S542-S548.*
Gong et al., "Study on the Reactive Crystallization of Cefadroxil", Zhongguo Kangshengsu Zazhi, vol. 30, No. 1, 2005. pp. 62-64. XP001536569.*
International Search Report for PCT/EP2007/054572, mailed Sep. 21, 2007.
Written Opinion for PCT/EP2007/054572, mailed Sep. 21, 2007.
Hendrix et al., "Synthesis of Related Substances of Cefadroxil", Arciv Der Pharmazie, vol. 327, 1994, pp. 805-807, XP009036665.
Parkkali et al., "Applying Image Analysis in the Observation of Recrystallization of Amorphous Cefadroxil" Pharmaceutical Development and Technology, vol. 5, 2000, pp. 433-438, XP009074802.
The Merck Index, 12*th* Edition, Merck Research Laboratories (1996), pp. 314-315 and REG-11.

* cited by examiner

*Primary Examiner* — Mark Berch
(74) *Attorney, Agent, or Firm* — Nixon & Vanderhye P.C.

(57) ABSTRACT

The present invention relates to a process for the preparation of cefadroxil in crystal form, comprising a) adding an aqueous solution of cefadroxil to a crystallization vessel and a titrant to keep a pH in the crystallization vessel of between 7 to 9; and b) lowering the pH in the crystallization vessel to a value of between 5 and 6.5 to obtain a suspension of the β-lactam compound in crystal form. The invention further relates to cefadroxil in crystal form obtainable by the process according to the present invention. The invention also relates to cefadroxil in crystal form with a CIE b value of below 12 when stored at a temperature of 25° C. for at least 1 month.

4 Claims, No Drawings

PROCESS FOR THE CRYSTALLISATION OF CEFADROXIL MONOHYDRATE

This application is the U.S. national phase of International Application No. PCT/EP2007/054572, filed 11 May 2007, which designated the U.S. and claims priority to Europe Application No. 06114240.2, filed 19 May 2006, the entire contents of each of which are hereby incorporated by reference.

The present invention relates to a process for the crystallisation of cefadroxil monohydrate and cefadroxil monohydrate in crystal form.

Cefadroxil is the name for the chemical compound 7-[D-α-amino-α-(p-hydroxyphenyl)-acetamido]desacetoxycephalosporanic acid. A process for the crystallisation of a β-lactam compound, such as cefadroxil, is for instance known from WO99/24441. WO 99/24441 discloses a process for the crystallisation of a β-lactam compound wherein a solution of said β-lactam compound and a corresponding titrant are simultaneously added to a crystallisation vessel to form a crystallisation mixture. In the process disclosed in WO99/55710 a crystalline β-lactam compound, for instance cefadroxil is prepared from a nitric acid solution by the addition of an alkaline solution to the nitric acid solution.

It was found that crystallisation of cefadroxil monohydrate by a crystallisation process known in the art resulted in agglomerates of cefadroxil monohydrate with a large particle size distribution, much colour and low colour stability. The aim of the present invention is to provide an alternative process for the crystallisation of cefadroxil monohydrate, which results in crystalline cefadroxil monohydrate with a small particle size distribution, little colour, and a high colour stability. The aim is achieved according to the invention by a process for the preparation of cefadroxil monohydrate in crystal form, comprising a) bringing an aqueous solution of cefadroxil monohydrate at a pH of between 7 to 9 with a suitable titrant; and b) lowering the pH to a value of between 5 and 6.5 to obtain a suspension of cefadroxil monohydrate in crystal form.

It was found that by keeping the pH of the aqueous solution at the desired value in step a) an explosion of cefadroxil monohydrate crystals was prevented which resulted in cefadroxil monohydrate crystals with a small particle size distribution, little colour, and a high colour stability.

As used herein cefadroxil monohydrate in crystal form with a small particle size distribution (psd) is defined as a psd of between 10 and 150 μm. The psd of the cefadroxil monohydrate in crystal form is preferably between 10 and 100 μm, more preferably between 20 and 80 μm, more preferably between 25 and 60 μm, most preferably between 30 and 50 μM.

As used herein, cefadroxil monohydrate in crystal form with little colour means that the cefadroxil crystals have a CIE b value of preferably below 6, preferably below 5.5, more preferably below 5, more preferably below 4.5, more preferably below 4, more preferably below 3 and usually above 1.

High colour stability means that the cefadroxil crystals have a CIE b value of below 12, more preferably below 11, more preferably below 10, more preferably below 9, more preferably below 8, more preferably below 7, more preferably below 6, more preferably below 5 and usually above 1, preferably when stored at a temperature of 25° C. for at least 1 month, more preferably for at least 2 months, more preferably for at least 3 months, more preferably for at least 4 months, more preferably for at least 5 months, more preferably for at least 6 months, more preferably for at least 7 months, more preferably for at least 8 months, more preferably for at least 9 months, more preferably for at least 10 months, more preferably for at least 11 months, more preferably for at least 12 months.

The aqueous solution of cefadroxil monohydrate used in step a) of the process of the present invention may be alkaline, for instance having a pH of between 8 and 9.5, for instance between 8.5 and 9, for instance between 8.6 and 8.9. Alternatively, the aqueous solution of cefadroxil monohydrate may be acidic, for instance having a pH of between 1 and 4, for instance between 1.5 and 3, for instance between 1.5 and 2.5.

The pH in step a) in the process according to the present invention is preferably brought to a pH of between 7 and 9, preferably between 7.1 and 8.9, preferably between 7.2 and 8.8, preferably between 7.3 and 8.7, more preferably between 7.4 and 8.6, more preferably between 7.5 and 8.5, more preferably between 7.6 and 8.4, more preferably between 7.7 and 8.3, more preferably between 7.8 and 8.2, more preferably between 7.9 and 8.1. A suitable titrant to bring the pH in step a) at a pH of between 7 and 9 may be any suitable acidic titrant such as formic acid, citric acid, acetic acid, sulphuric acid or hydrochloric acid. A suitable titrant is preferably formic acid. Alternatively a suitable titrant to bring the pH at a value of between 7 and 9 may be any suitable alkaline titrant such as sodium hydroxide, potassium hydroxide, ammonium hydroxide, or an amine, for instance a monoamine, such as tertiary butylamine, tertiary octylamine, benzhydrylamine or a diamine, for instance N,N'-diisopropylethylenediamine, N,N, N',N'-tetramethyl-1,2-diaminoethane or bis(2-(dimethylamino)ethyl)ether. The skilled man understands that depending on the pH of the aqueous solution of cefadroxil monohydrate used in step a) of the process of the present invention an acidic or alkaline titrant may be needed to arrive at the desired pH value.

When adding the aqueous solution of cefadroxil monohydrate to the crystallisation vessel, the crystallisation vessel may comprise a small amount of water. The crystallisation may also comprise a small amount of cefadroxil monohydrate in crystal form, serving as a seed for the cefadroxil monohydrate in the aqueous solution.

The pH in step b) in the process according to the present invention is preferably lowered to a pH value between 5.2 and 6.4, preferably between 5.4 and 6.3, preferably between 5.6 and 6.2, more preferably between 5.8 and 6.1.

During step b), the pH may be lowered using any suitable titrant, for instance, formic acid, citric acid, acetic acid, sulphuric acid or hydrochloric acid. Preferably, formic acid is used for decreasing the pH in step b).

Lowering the pH in step b) of the process according to the present invention may be carried out within any suitable period of time. Preferably, lowering the pH in step b) may occur within a period of time of between 5 min and 4 hrs, preferably between 10 min and 3 hrs, preferably between 15 min and 2 hrs, preferably between 20 min and 60 min.

The aqueous solution of cefadroxil monohydrate in the step a) in the process according to the present invention may be obtained from any suitable chemical or enzymatic acylation process for the synthesis of cefadroxil. A chemical acylation process for the synthesis of cefadroxil is for instance disclosed in EP 0 295 333. Preferably, the aqueous solution of cefadroxil is obtained from an enzymatic process for the synthesis of cefadroxil, wherein 7-amino-3-desacetoxycephalosporanic acid (7-ADCA) is acylated with a D-p-hydroxyphenylglycine (HPG) in activated form in the presence of a suitable acylase in free or immobilised form. HPG in activated form may for instance be an amide or an ester of HPG, for instance methylester. Processes for the enzymatic synthesis of cefadroxil are described in EP 0 865 443 B1, EP 0771 357 B1, EP 537 255 and WO 99/20786, which are herein incorporated by reference.

Adding the aqueous solution of cefadroxil monohydrate to a crystallisation vessel in step a) of the process according to the invention may be carried out during any suitable period of time, depending for instance on the total volume of aqueous solution to be added. A suitable period of time may range between 5 min and 4 hrs, for instance between 10 min and 3 h, for instance between 15 min and 2 hrs, for instance between 20 min and 1.5 hrs.

Adding the aqueous solution of cefadroxil monohydrate to a crystallisation vessel in step a) and lowering the pH in step b) in the process according to the present invention may be carried out at any suitable temperature. Preferably, the temperature in step a) is carried out at a temperature of between 5 and 25° C., more preferably between 10 and 20° C. Preferably, the temperature in step b) is carried out at a temperature of between 5 and 25° C., more preferably between 10 and 20° C. In the process according to the present invention, cefadroxil monohydrate crystals may be formed from the aqueous solution during each step. Depending for instance on the temperature and pH value, the amount of cefadroxil monohydrate in crystal form prepared may be higher or lower during any of the steps a) or b). Usually, a major amount of cefadroxil monohydrate in crystal form is prepared from the aqueous solution during step b).

The suspension of cefadroxil monohydrate in crystal form obtained in step b) in the process according to the invention may be stirred during a suitable period of time, for instance during 10 to 120 min, preferably during 15 to 90 min, preferably during 20 to 60 min, preferably during 25 to 50 min. It was found that stirring the suspension of cefadroxil monohydrate in crystal form resulted in an increased yield of the cefadroxil monohydrate in crystal form. Cefadroxil monohydrate in crystal form may be isolated from the suspension by any suitable method known in the art. Cefadroxil monohydrate in crystal form may for instance be isolated from the suspension by filtration or centrifugation. Usually the cefadroxil monohydrate crystals are washed with water to remove impurities.

Isolation of the cefadroxil monohydrate crystals may further comprise drying the crystals at a temperature of, for instance between 40 and 50° C. Preferably, the β-lactam crystals are washed with acetone to remove a major amount of water, prior to drying.

The present invention also relates to cefadroxil monohydrate in crystal form obtainable by the process according to the present invention. It was surprisingly found that the cefadroxil monohydrate in crystal form obtainable by the process according to the present invention has a CIE b value of below 6, preferably below 5.5, more preferably below 5, more preferably below 4.5, more preferably below 4, more preferably below 3 and usually above 1.

It was also surprisingly found that the cefadroxil monohydrate crystals were very stable in the colour stability test. It was found that the cefadroxil monohydrate crystals obtainable by the process according to the present invention have a CIE b value of below 12, more preferably below 11, more preferably below 10, more preferably below 9, more preferably below 8, more preferably below 7, more preferably below 6, more preferably below 5 and usually above 1, preferably when stored at a temperature of 25° C. for at least 1 month, more preferably for at least 2 months, more preferably for at least 3 months, more preferably for at least 4 months, more preferably for at least 5 months, more preferably for at least 6 months, more preferably for at least 7 months, more preferably for at least 8 months, more preferably for at least 9 months, more preferably for at least 10 months, more preferably for at least 11 months, more preferably for at least 12 months.

In addition, the cefadroxil monohydrate in crystal form according to the present invention has a particle size distribution of below 150 µm, preferably below 100 µm and preferably above 10 µm. The psd of the cefadroxil monohydrate in crystal form is preferably between 10 and 150 µm, more preferably 10 and 100 µm, more preferably between 20 and 80 µm, more preferably between 25 and 60 µm, most preferably between 30 and 50 µM.

Materials and Methods

Determination of the CIE b Value

CIE is an abbreviation for the French title of the International Commission on Illumination: "Commission Internationale de l'Eclairage". The CIE b is a measure to determine the colour of crystals, which is a known technology for the skilled man in the art. An overview of the fundamentals of the CIE colorimetry system is given in Ohno, Y., Paper for IS&T NI016 Conference, Vancouver, Canada, Oct. 16-20, 2000, p. 1-5.

The CIE b value was determined using a X-Rite® 918 apparatus (X-Rite Incorporated, 4300 44th St. SE, Grand Rapids, Mich. 49512 USA). A sample of 2 g of cefadroxil crystals was placed at the appropriate place of the apparatus and the CIE b value was read. The average of two separate readings was calculated.

EXAMPLES

Preparation of a Cefadroxil Monohydrate Solution

Cefadroxil monohydrate was obtained by an enzymatic process for the synthesis of cefadroxil, wherein 7-amino-3-desacetoxycephalosporanic acid (7-ADCA) was acylated with D-p-hydroxyphenylglycinemethyl ester in the presence of immobilised Pen G acylase as described in WO 99/20786.

A sample of 500 g of mother liquor and water washings was taken from the enzymatic reactor at the end of the condensation step. The sample contained 16.34 (w/w) of dissolved cefadroxil monohydrate. The pH was 8.7-8.8

Reference Experiment A: One-Step Crystallisation

A 500 g sample of the cefadroxil monohydrate solution prepared as described above was dosed into a crystallisation reactor within 25 to 70 minutes. The crystallisation reactor contained a small amount of water to allow stirring. The pH was kept at a value of between 7.10 and 7.30 with formic acid at a temperature of between 7 to 10° C. The suspension of cefadroxil monohydrate was stirred for 30 min. The cefadroxil monohydrate suspension was centrifuged and dried. The colour of the cefadroxil monohydrate agglomerates at t=0 was determined as described below. The CIE b value was 6.2.

Example 1

Two-Step Crystallisation of Cefadroxil Monohydrate

Step a)

5 g of cefadroxil monohydrate (used as a seed) and 60 ml of fresh water (pH=5.50-5.70) were loaded into a crystallisation vessel and the temperature was adjusted to 15° C. A 500 g sample of the cefadroxil monohydrate solution prepared as described above was dosed into the crystallisation vessel within 45 minutes. The pH was kept at 7.9 by titration with 6.9 ml of formic acid (85% v/v).
Step b)
2.5 ml of formic acid was added to the suspension obtained in step (a) in such a way that the pH decreased to 6.0 in 30 minutes. The cefadroxil monohydrate suspension thus obtained was stirred for 30 min. The suspension was filtered and the cake was washed with 50 ml of water followed by 34 ml acetone. After drying, 76.4 g of cefadroxil monohydrate was obtained (84.0 w/w % yield).

The CIE b value of the cefadroxil monohydrate crystals was 4.68.

Example 2

Two-Step Crystallisation of Cefadroxil Monohydrate

Step a)
33 ml of a 500 g sample of the cefadroxil monohydrate solution prepared as described above, and 27 ml of fresh water, were added to a crystallisation reactor. The temperature was adjusted to 15° C. Subsequently the remaining part of the 500 g sample of cefadroxil monohydrate solution was dosed into the crystallisation reactor in 35 minutes. The pH was kept at 7.9 by titration with 4.5 ml of formic acid (85% v/v).
Step b)
8.4 ml of formic acid (85% v/v) were added to the cefadroxil monohydrate solution obtained in step (a) in such a way that the pH decreased to 6.0 in 30 minutes. The obtained cefadroxil monohydrate suspension was stirred for 30 min. The suspension was filtered and the cake was washed with 50 ml of water followed by 34 ml acetone. After drying, 72.8 g of cefadroxil was obtained (84.7% (w/w) yield). The CIE b value of the cefadroxil monohydrate crystals was 4.52.

Example 3

Colour Stability Test 4.1 Stress Conditions: Storage at 40° C.

Cefadroxil (CDX) monohydrate crystals obtained by the one-step crystallisation process of the Reference Experiment A and the two-step crystallisation process according to the present invention were stored at a temperature of 40° C. The CIE b values of the different cefadroxil monohydrate crystals were determined at different time intervals as indicated in Table 1. CDX (1)-(3) were obtained from 3 different crystallisation processes.

TABLE 1

| Weeks | CIE b of CDX crystals obtained by the one-step crystallisation process | CIE b of CDX crystals obtained by the two-step crystallisation process | | |
|---|---|---|---|---|
| | | CDX (1) | CDX (2) | CDX (3) |
| 0 | 6.2 | 4.8 | 4.4 | 3.1 |
| 2 | 10.0 | — | 4.8 | 3.0 |
| 4 | 13.2 | 6.6 | 5.1 | 4.6 |
| 6 | 15.6 | — | — | — |
| 8 | 17.0 | 9.1 | — | — |
| 12 | 14.2 | 10.4 | — | — |

TABLE 1-continued

| Weeks | CIE b of CDX crystals obtained by the one-step crystallisation process | CIE b of CDX crystals obtained by the two-step crystallisation process | | |
|---|---|---|---|---|
| | | CDX (1) | CDX (2) | CDX (3) |
| 14 | 18.2 | — | — | — |
| 18 | 18.6 | — | — | — |
| 20 | 19.1 | 12.4 | — | — |
| 24 | 20.0 | 12.9 | — | — |

—: not determined 4.2 Storage at 25° C.

The cefadroxil monohydrate crystals obtained with the one-step crystallisation process of Reference experiment A and a two-step crystallisation process according to the present invention were stored at 25° C. The CIE b value was determined at different time intervals as indicated in Table 2.

TABLE 2

Comparison colour stability at 25° C.

| Months | CIE b one-step crystallization process | CIE b two-step crystallization process |
|---|---|---|
| 0 | 6.2 | 4.8 |
| 3 | 14.0 | 5.8 |
| 6 | 14.7 | 6.0 |
| 9 | 15.1 | 6.3 |
| 12 | 15.5 | — |
| 18 | 17.7 | — |

—: not determined

The results in table 1 and 2 show that the CIE b values of the cefadroxil monohydrate crystals obtained with the two-step crystallisation process according to the present invention remained lower than the CIE b values of cefadroxil monohydrate crystals obtained with the one-step crystallisation process when the cefadroxil monohydrate crystals were stored at 25° C. and 40° C. Therefore, colour stability of the cefadroxil monohydrate crystals prepared with the process according to the present invention was higher than prepared with the one-step crystallisation process of Reference experiment A.

The invention claimed is:

1. A process for the preparation of cefadroxil monohydrate in crystal form, comprising:
   a) bringing an aqueous solution of cefadroxil monohydrate to a pH of between 7 to 9 with a suitable titrant;
   b) lowering the pH to a value of between 5 and 6.5 to obtain a suspension of cefadroxil monohydrate in crystal form; and
   c) isolating the cefadroxil monohydrate in crystal form from the suspension obtained in step b).

2. The process according to claim 1, wherein step a) and step b) are carried out at a temperature of between 5 and 25° C.

3. The process according to claim 1, wherein lowering the pH in step b) is carried out within a period of time of between 20 to 60 min.

4. The process according to claim 1, wherein the suspension of the cefadroxil monohydrate in crystal form obtained in step b) is stirred for 10 to 120 min.

* * * * *